United States Patent [19]

Eggers

[11] Patent Number: 5,693,045
[45] Date of Patent: Dec. 2, 1997

[54] ELECTROSURGICAL GENERATOR CABLE

[75] Inventor: Philip E. Eggers, Dublin, Ohio

[73] Assignee: Hemostatic Surgery Corporation, Grand Cayman, Cayman Islands

[21] Appl. No.: 486,736

[22] Filed: Jun. 7, 1995

[51] Int. Cl.$^6$ ................................ A61B 17/36
[52] U.S. Cl. ................ 606/50; 606/48; 606/32; 174/36
[58] Field of Search ............. 606/32–53; 607/88–89, 607/96, 98–99, 101–102, 145, 148, 150, 154; 174/36; 307/52, 62

[56] References Cited

U.S. PATENT DOCUMENTS

| | | | |
|---|---|---|---|
| 1,586,645 | 6/1926 | Bierman . | |
| 3,651,811 | 3/1972 | Hildebrandt et al. | 128/303.17 |
| 3,685,518 | 8/1972 | Beurle et al. | 128/303.16 |
| 3,730,188 | 5/1973 | Ellman | 128/303.14 |
| 3,875,945 | 4/1975 | Friedman | 128/303.14 |
| 3,980,085 | 9/1976 | Ikuno | 128/303.17 |
| 4,005,714 | 2/1977 | Hiltebrandt | 128/303.17 |
| 4,030,501 | 6/1977 | Archibald | 128/303.14 |
| 4,041,952 | 8/1977 | Morrison, Jr. | 128/303.13 |
| 4,054,143 | 10/1977 | Bauer | 128/303.14 |
| 4,092,986 | 6/1978 | Schneiderman | 128/303.14 |
| 4,154,240 | 5/1979 | Ikuno et al. | 128/303.14 |
| 4,196,734 | 4/1980 | Harris | 128/303.1 |
| 4,232,676 | 11/1980 | Herczog | 128/303.14 |
| 4,338,940 | 7/1982 | Ikuno | 128/303.14 |
| 4,370,980 | 2/1983 | Lottick | 128/303.17 |
| 4,492,231 | 1/1985 | Auth | 128/303.17 |
| 4,590,934 | 5/1986 | Malis et al. | 128/303.14 |
| 4,651,734 | 3/1987 | Doss et al. | 128/303.14 |
| 4,657,016 | 4/1987 | Garito et al. | 128/303.13 |
| 4,658,819 | 4/1987 | Harris et al. | 128/303.13 |
| 4,685,459 | 8/1987 | Koch et al. | 128/303.17 |
| 4,752,864 | 6/1988 | Clappier | 363/86 |
| 4,862,890 | 9/1989 | Stasz et al. | 128/303.14 |
| 4,903,696 | 2/1990 | Stasz et al. | 606/37 |
| 4,938,761 | 7/1990 | Ensslin | 606/51 |
| 4,958,539 | 9/1990 | Stasz et al. | 76/104.1 |
| 4,961,739 | 10/1990 | Thompson | 606/37 |
| 4,969,885 | 11/1990 | Farin | 606/38 |

FOREIGN PATENT DOCUMENTS

| | | | |
|---|---|---|---|
| 854366 | 8/1981 | U.S.S.R. | A61B 3/06 |
| 2 037 167 | 7/1980 | United Kingdom | A61B 17/36 |
| 2 066 104 | 7/1981 | United Kingdom | A61B 17/32 |
| 2 161 082 | 1/1986 | United Kingdom | A61B 17/36 |
| 2 213 381 | 8/1989 | United Kingdom | A61B 17/36 |

OTHER PUBLICATIONS

"Electrosurgical Units", Evaluation, *Health Devices*, Sep.–Oct. 1987, pp. 291–342.

*Primary Examiner*—Robert L. Nasser
*Assistant Examiner*—Ryan Carter
*Attorney, Agent, or Firm*—Fish & Neave; Nicola A. Pisano; Michael J. DeHaemer

[57] ABSTRACT

An adaptor cable and methods are provided for use with electrosurgical bipolar instruments and standard commercially available electrosurgical generators that reduce arcing. The adaptor cable limits the peak-to-peak voltage developed between the electrodes of the electrosurgical instrument by providing a minimum load impedance between the output terminals of the electrosurgical generator.

10 Claims, 2 Drawing Sheets

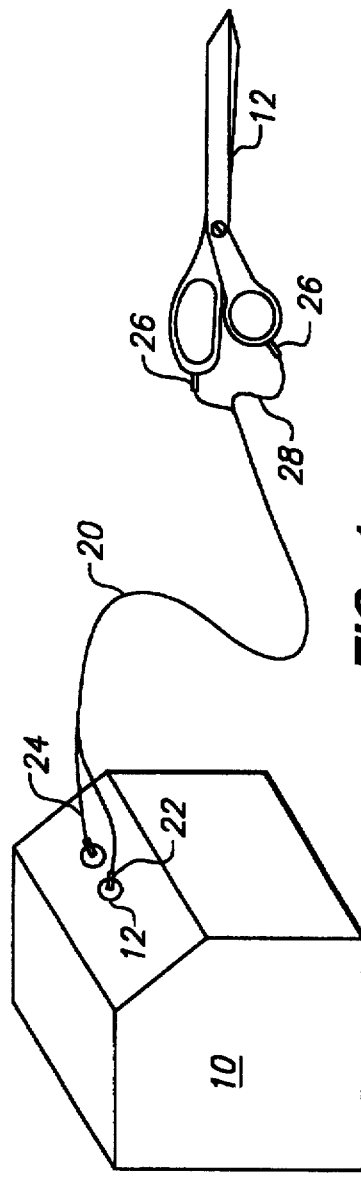
FIG. 1
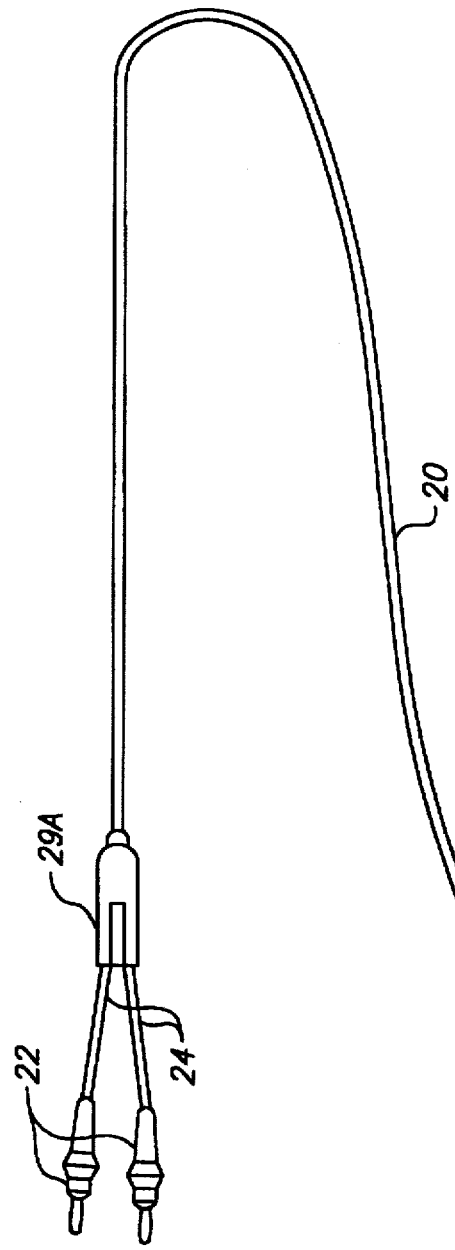
FIG. 2
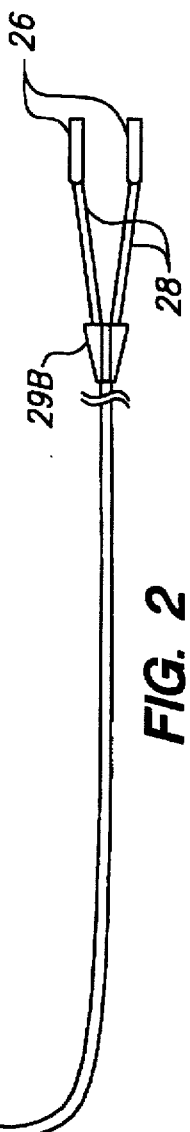

ELECTROSURGICAL GENERATOR CABLE

This invention relates to cables for use with conventional electrosurgical generators (ESG) to provide voltage output waveforms effective in reducing coagulum buildup, and to alleviate sticking, on hemostatic electrosurgical instruments. More particularly this invention relates to adaptor cables which limit the voltage present between electrodes of an electrosurgical instrument when not in contact with tissue.

BACKGROUND OF THE INVENTION

Hemostatic bipolar electrosurgical techniques are known for reducing bleeding from incised tissue prior to, during, and subsequent to incision. Such techniques generally pass a high voltage-high frequency current through a patient's tissue between two electrodes for cutting and coagulating the tissue. This current causes joulean heating of the tissue as a function of the current density and the impedance of the tissue. Heat deposited in the tissue coagulates the blood in the vessels contained in the tissue, thus reducing the blood flow from severed vessels and capillaries.

Previously known ESGs typically provide monopolar and bipolar modes of operation in which they supply high frequency (above 100 kHz) alternating-current (AC) voltages in the range of 150 to 5000 volts peak-to-peak (or higher) at power ratings of less than 400 watts. Examples of such generators are provided in Malis et al. U.S. Pat. No. 4,590,934, Schneiderman U.S. Pat. No. 4,092,986, Farin U.S. Pat. No. 4,969,885. See also, for example, the Operator's Manual for the Valleylab Force 2® and Force 4® generators. The bipolar output voltage of these generators increases with increasing load impedance, with the largest peak-to-peak voltages occurring under open circuit conditions, i.e. when the electrosurgical instrument is energized before being brought into contact with tissue.

This voltage increase is not important in previously known bipolar instruments such as forceps since the insulation between the two "legs" of the forceps is more than adequate to handle the 800 to 2500 $V_{pp}$ than can be generated by bipolar electrosurgical units when operated in the open circuit condition (i.e., not in contact with tissue). As soon as the bipolar device (e.g., forceps) grasps tissue, however, the load becomes much lower, in the range 50 to several hundred ohms.

Newer bipolar devices are now being introduced to market that incorporate closely spaced bipolar electrodes. For example, bipolar scissors are now available wherein the scissor members are spaced apart by a distance of only 3 to 6 mils using a ceramic insulation layer. Also, such devices may include other components such as pivot screws which have a relatively thin insulation layer, on the order of several mils. These devices preferably employ a voltage output in a range generally not exceeding 300 to 400 volts (peak to peak).

The use of large peak-to-peak voltages in some instruments has been found to lead to arcing between the tissue and the instrument when the instrument is first brought into contact with the tissue. Such arcing may cause deep tissue necrosis and cause the tissue to stick to the instrument. Indeed, such effects may even occur in some previously known low voltage systems, for example, those described in Herczog U.S. Pat. No. 4,232,676, and Auth U.S. Pat. No. 4,492,231.

To remedy this situation, special low voltage ESGs and adaptors have been developed that limit the peak voltages supplied to the electrosurgical instrument, as described in copending U.S. patent application Ser. No. 08/275,598, entitled "Electrosurgical Generator Adaptors", filed Jul. 15, 1994, and U.S. patent application Ser. No. 08/210,090, entitled "Electrosurgical Apparatus For Employing Constant Voltage And Methods Of Use," filed Mar. 17, 1994, which is a continuation of U.S. patent application Ser. No. 07/877,533, filed Jun. 7, 1991.

The foregoing applications describe methods and custom ESGs and adaptors utilizing electronic circuitry to "clip" the peak to peak voltage when it exceeds a preselected value. For example, the apparatus described in the above-referenced applications clips the bipolar output voltage, for example, whenever the surgeon energizes the bipolar scissors before the scissors are in contact with the tissue (i.e., open circuit condition). Once the scissors engage tissue, the load (i.e., tissue) resistance is sufficiently low that the output voltage is below the preselected clipping threshold (e.g., 400 $V_{pp}$).

Adaptors described in the foregoing applications employ electronic circuits with active electronic components mounted on a heat sink, and contained within an approximately 1.5"×1.5"×6" long electrically insulating module. The adaptors require an appropriate adaptor plug to allow connection to the bipolar output of the various electrosurgical generators available.

While the above-described special purpose ESGs provide excellent results for new system installations, they do not permit the ready modification or adaptation of the large installed base of more conventional generators. Also, while the above-described adaptors provide excellent performance when used to retrofit previously known electrosurgical generators, the use of active circuit components (e.g., transformers and transistors) and heat sinks in those devices tends to increase the size, cost and manufacturing effort for such adaptors.

It would therefore be desirable to provide a simple to use, low-cost adaptor for use with standard commercially available ESGs that would reduce problems associated with excessive open circuit voltages.

It further would be desirable to provide an adaptor that could be connected between the bipolar output jacks of standard commercially available ESGs and most electrosurgical instruments to limit the peak-to-peak voltage supplied to the instruments to reduce electrical arcing between the electrodes of the instrument, and between the electrodes and tissue.

It would additionally be desirable to provide an adaptor that is readily manufacturable, and that avoids the use of active circuit components and dedicated heat sinks.

SUMMARY OF THE INVENTION

In view of the foregoing, it is an object of this invention to provide a simple to use, low-cost adaptor for use with standard commercially available ESGs that reduces problems associated with excessive peak-to-peak open circuit output voltages.

It is a further object of the present invention to provide adaptors that can be connected between the monopolar or bipolar output jacks of standard commercially available ESGs and most electrosurgical instruments to limit the peak-to-peak voltage supplied to the instruments, to thereby reduce electrical arcing between the electrodes of the instrument, and between the electrodes and tissue.

It is yet another object of this invention to provide an adaptor that is readily manufacturable, and that avoids the use of active circuit components and dedicated heat sinks.

These and other objects are accomplished in accordance with the principles of the present invention by providing an adaptor cable, for use with standard commercially available power supplies, that limits the maximum voltage applied to a bipolar device by never allowing the load resistance to be more than a preselected value. For example, a load resistance of 600 ohms connected to the bipolar output of most convention electrosurgical generators limits the maximum output voltage to 350 to 500 V peak to peak—a voltage range sufficiently low to prevent severe arcing and/or damage to the bipolar instrument.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which:

FIG. 1 is an elevated perspective view of an adaptor cable constructed in accordance with the present invention, coupled between a standard electrosurgical generator and an electrosurgical instrument;

FIG. 2 is an enlarged illustrative view of the adaptor cable of FIG. 1;

DETAILED DESCRIPTION OF THE INVENTION

Figure 3:
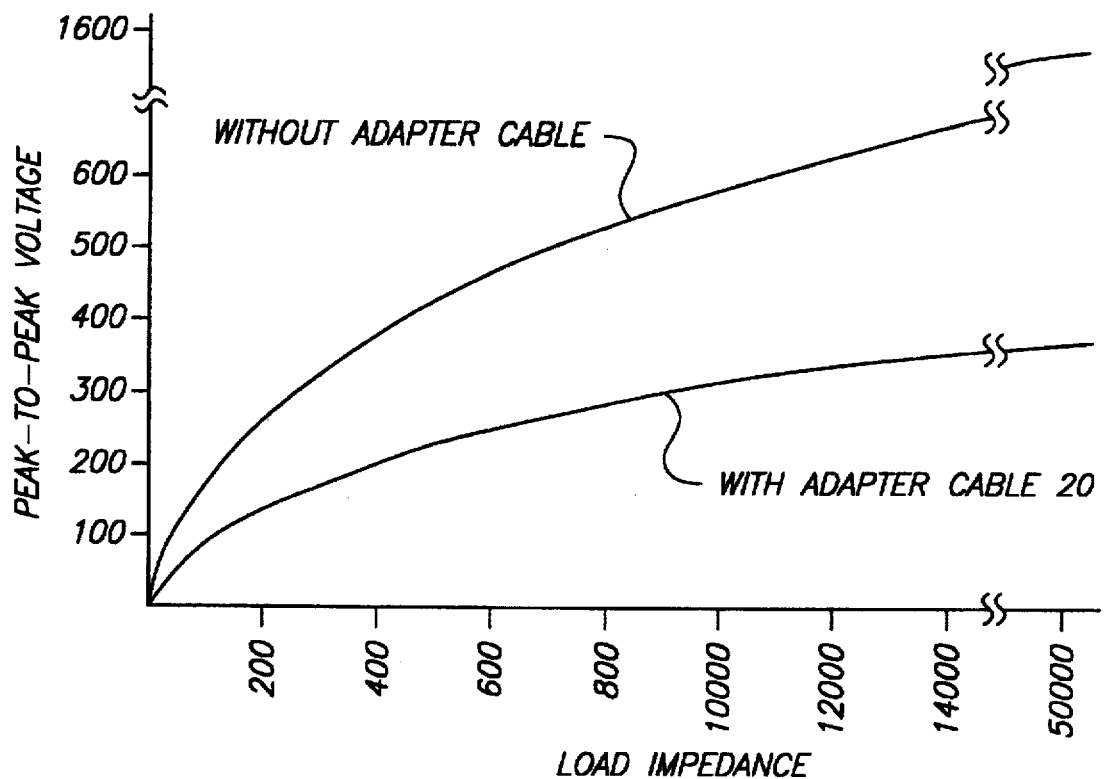
FIG. 3 is a comparison of the electrical output characteristics of an illustrative electrosurgical generator with and without the adaptor cable of the present invention.

Referring to FIGS. 1 and 2, adaptor cable 20 of the present invention is shown coupled between conventional electrosurgical generator 10 and bipolar instrument 12. As described hereinafter, adaptor cable 20 reduces coagulum buildup, arcing, and sticking on electrosurgical instrument 12 by limiting the peak open-circuit voltage (developed when electrosurgical instrument 12 is energized before contacting the tissue) supplied to the instrument electrodes (and tissue) to about 200 Vpeak (400 Vpeak-to-peak).

Conventional ESG 10 is shown having bipolar output jacks 14, and may be, for example, a Valleylab Force 4®, Force 2® or other similar ESG such as those commercially available from Valleylab, Aspen, Clinical Technology or Neomed, while bipolar instrument 12 may be bipolar scissors such as described in U.S. Pat. No. 5,324,289. Generator 10 preferably is capable of developing in the range of at least 50 watts power in the bipolar mode and have maximum open-circuit peak-to-peak voltages less than about 1500 V in bipolar mode.

Adaptor cable 20 is preferably connected to the bipolar output jacks 14 of conventional ESG 10 by plugs 22, which may be banana plugs or other suitable connection means, disposed at the ends of leads 24. Adaptor cable 20 likewise includes connectors 26, disposed on leads 28, that enable adaptor cable 20 to be coupled to the electrosurgical instrument 12. Leads 24 and 28 emanate from the main length of cable 20 at junctions 29A and 29B.

Adaptor cable 20 accepts a high frequency high voltage output waveform (e.g., about 1500 Vpeak-to-peak) from generator 10 via bipolar output jacks 14 and supplies a waveform to electrosurgical instrument 12 having a voltage which does not exceed about 350–400 Vpeak-to-peak.

Adaptor cable 20 according to the principles of the present invention suppresses any high open-circuit voltages, occurring for example, when electrosurgical instrument 12 is energized before it contacts a patient's tissue.

Adaptor cable 20 limits the maximum voltage applied to a bipolar device so that the load resistance does not exceed a preselected value. For example, if a load resistance of 600 ohms is connected to the bipolar output of most convention electrosurgical generators, the maximum output voltage is limited to 350 to 500 V peak to peak. This reduced voltage range is sufficiently low to prevent severe arcing and/or damage to bipolar instrument 12.

At the applied voltages of typical electrosurgical generators, operating at maximum set point, a 600 ohm load will result in the dissipation of 15 to 20 watts. This power dissipation only occurs, however, during those periods while the surgeon is energizing the bipolar instrument but not in contact with tissue. Therefore, the duty cycle for such a heating rate would not be greater than 25% and hence the continuous or average heating rate would be less than about 4 to 5 watts. For a 0.2 inch (5 mm) diameter adaptor cable, this average heating rate would lead to a maximum cable surface temperature rise of 4.5° to 6.0° C.

During normal use of bipolar instrument 12 (i.e., while in contact with tissue), the output voltage from generator 10 will be much lower than described above, hence the power dissipated in a 600 ohm resistance will be much lower. For example, at a tissue load of 60 ohms, the total power dissipated in a 600 ohm parallel load would be 10.4 watts in place of 16 watts under open circuit condition (i.e., bipolar instrument 12 not in contact with tissue). At 25% duty cycle, this translates to approximately 2.6 watts or a 2.9° C. temperature rise.

As shown in FIG. 3, the output voltage of a typical ESG increases with increasing load impedance. When the electrodes of an electrosurgical instrument are not in contact with tissue, the load impedance presented to the output of ESG 10 is essentially an infinite impedance, or open circuit. Under open circuit conditions the output of ESG 10 may approach several thousand volts. FIG. 3 also shows the limiting effect the present invention has on the peak-to-peak output voltage of ESG 10, limiting the peak-to-peak voltage to about 400 volts, for example.

Figure 4:
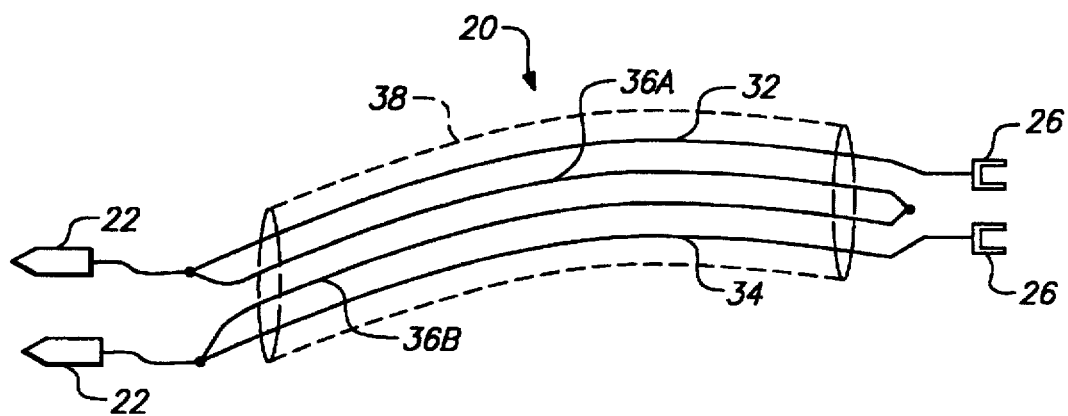
FIG. 4 is a cut-away view of an adaptor cable manufactured in accordance with the principles of the present invention.

Referring now to FIG. 4, a preferred embodiment of the present invention is described. Adaptor cable 20 consists of conductors 32 and 34 coupled, respectively, between plugs 22 and connectors 26. As shown in FIG. 4, a loop of high electrical resistivity wire comprising strands 36A and 36B runs the length of adaptor cable 20. Conductors 32 and 34 and resistive wires 36A and 36B are each electrically insulated from one another other, for example, by suitable teflon or silicon coatings (not shown). Outer covering 38 also comprises an electrically insulative material that serves to protect and insulate conductors 32 and 34 and resistive wires 36A and 36B, for example, a silicone rubber material.

In accordance with the present invention, to maintain the temperature rise as low as possible, the loop of high electrical resistance wire 36A, 36B may comprise, for example, a 36 gauge 316 stainless steel wire (for example, as manufactured by Cooher Wire Co.) having a resistance of about 18.4 ohms/foot at 25° C. Based on a cable length of 5 meters (preferred for international markets), the total resistance of a loop extending down and back the 5 meter cable length is:

5 meter=16.4 feet $R_T = 2 \times 16.4 \text{ ft} \times 18.4 \text{ ohms/ft} = 604 \text{ ohms}$ Using 38 gauge stainless steel 316 wire, the total resistance would be approximately 1000 ohms.

The resistance of loop 36A, 36B may be selected depending upon the particular output characteristics of the electrosurgical generator with which bipolar instrument 12 is to be used. Applicant expects that a loop of resistive wire 36A, 36B having a resistance of 600 ohms will be suitable for most electrosurgical generators. However, if a particular generator operates at too high an output voltage with a 600 ohm load (e.g., greater than 500 V peak to peak), then a lower resistance would be desired. Likewise, some generators may allow the use of a higher load resistance.

The adaptor cable of the present invention therefore provides an effective load on the electrosurgical generator 10 by adding a loop of high resistance wire (wires 36A, 36B), to an otherwise conventional medical grade cable for use with bipolar instruments and conventional electrosurgical generators. As seen in FIG. 4, the high resistance wire is connected in parallel with the bipolar instrument so that the load resistance applied to the electrosurgical generator is never more than the resistance of the loop of wire within the cable (e.g., 400 to 1000 ohms). By extending the resistance wire over the major length of adaptor cable 20, the heat generated in the adaptor cable is dissipated over a large volume, and therefore the temperature rise is maintained adequately low.

Adaptor cable 20 may be readily manufactured by removing a portion of outer covering 38; the electrical insulation is then stripped from conductors 32 and 34 and resistive wires 36A and 36B. Conductors 32 and 34 are then coupled to plugs 22 and to connectors 26, while resistive wires 36A and 36B are coupled to conductors 32 and 32 as shown in FIG. 4. The remaining stripped ends of resistive wires 36A and 36B are coupled to each other. Connections between resistive wires 36A, 36B and conductors 32 and 34 may then be sealed, for example, by encasement in junctions 29A and 29B (seen in FIG. 2), to protect the wires and connections.

This present invention provides valuable benefits in controlling arcing and reducing the risk of tissue damage/instrument damage, while providing the simplicity of ordinary conventional medical grade cables for use with bipolar electrosurgical instruments.

One skilled in the art will appreciate that the present invention can be practiced by other than the described embodiments, which are presented for purposes of illustration and not of limitation, and that the present invention is limited only by the claims that follow.

What is claimed is:

1. An adaptor cable for coupling a bipolar electrosurgical instrument having a pair of electrodes to an electrosurgical generator having bipolar output terminals, the adaptor cable comprising:

first and second conductors adapted for coupling the electrodes of the electrosurgical instrument to the bipolar output terminals of the electrosurgical generator; and at least one resistive wire coupled between the first and second conductors, wherein the at least one resistive wire limits the peak voltages developed between the bipolar output terminals.

2. The adaptor cable of claim 1 wherein the adaptor cable has a length and the at least one resistive wire comprises a loop that extends for the length.

3. The adaptor cable of claim 2 wherein the loop comprises first and second resistive wires coupled in series between the first and second conductors.

4. The adaptor cable of claim 1 wherein the at least one resistive wire comprises first and second resistive wires coupled in parallel with respect to the first and second conductors.

5. An adaptor cable for coupling a bipolar electrosurgical instrument having a pair of electrodes to an electrosurgical generator having bipolar output terminals, the adaptor cable having a length and comprising:

first and second conductors adapted for coupling the electrodes of the bipolar electrosurgical instrument to the bipolar output terminals;

at least one resistive wire coupled between the first and second conductors, wherein the at least one resistive wire is distributed along a portion of the length of the adaptor cable and limits the peak voltages developed between the bipolar output terminals.

6. The adaptor cable of claim 5 wherein the at least one resistive wire comprises a loop of 316 stainless steel wire.

7. The adaptor cable of claim 6 wherein the 316 stainless steel wire is between about 36 gauge and about 38 gauge.

8. The adaptor cable of claim 7 wherein the at least one resistive wire comprises a respective wire running the length of the adaptor cable.

9. A method of limiting peak voltages between electrodes of a bipolar electrosurgical instrument coupled to output terminals of a standard electrosurgical generator, the method comprising the steps of:

providing first and second conductors adapted for coupling the electrodes to the output terminals;

providing at least one resistive wire coupled between the first and second conductors; and coupling the first and second conductors between the electrodes and the output terminals to limit peak voltages developed between the bipolar output terminals.

10. The method of claim 9 wherein the at least one resistive wire comprises a loop of 316 stainless steel wire.

* * * * *